US005698739A

United States Patent [19]

Sovak

[11] Patent Number: 5,698,739

[45] Date of Patent: Dec. 16, 1997

[54] CARBOXAMIDE NON-IONIC CONTRAST MEDIA

[75] Inventor: Milos Sovak, Rancho Santa Fe, Calif.

[73] Assignee: Schering Aktiengesellschaft, Berlin, Germany

[21] Appl. No.: 462,047

[22] Filed: Jun. 5, 1995

Related U.S. Application Data

[63] Continuation-in-part of Ser. No. 365,185, Dec. 28, 1994, abandoned, which is a continuation of Ser. No. 548,416, Jul. 5, 1990, abandoned, which is a continuation-in-part of Ser. No. 431,527, Nov. 3, 1989, abandoned, which is a continuation-in-part of Ser. No. 375,714, Jul. 5, 1989, abandoned.

[51] Int. Cl.[6] .......... C07C 233/77

[52] U.S. Cl. .......... 564/153; 424/9.452

[58] Field of Search .......... 564/153; 424/9.452

[56] References Cited

U.S. PATENT DOCUMENTS

| | | |
|---|---|---|
| 3,701,771 | 10/1972 | Almen et al. . |
| 4,001,323 | 1/1977 | Felder et al. . |
| 4,021,481 | 5/1977 | Almen et al. . |
| 4,250,113 | 2/1981 | Nordal et al. . |
| 4,278,654 | 7/1981 | Rakli et al. . |
| 4,341,756 | 7/1982 | Sovak et al. . |
| 4,364,921 | 12/1982 | Speck et al. . |
| 4,396,598 | 8/1983 | Lin . |
| 4,426,371 | 1/1984 | Pfeiffer et al. . |
| 4,547,357 | 10/1985 | Pfeiffer et al. . |
| 4,584,401 | 4/1986 | Sovak et al. . |
| 5,047,228 | 9/1991 | Gries et al. .......... 424/5 |

FOREIGN PATENT DOCUMENTS

| | | |
|---|---|---|
| 1321591 | 6/1973 | United Kingdom . |

OTHER PUBLICATIONS

Grandi et al., Chem. Abs. 99:211976e (1983).

Brandamante et al. chem. Abs. 108:5483t (1988).

Grandi et al., Biomediaal Mass Spectro, vol. 10(1), pp. 17–23 (1983).

Bradamante et al., Mag. Res. in Chem., vol. 25, pp. 283–292 (1987).

Felder et al., Chem. Abs. 110(21): 192447k (1989).

*Primary Examiner*—Brian M. Burn

*Attorney, Agent, or Firm*—Millen, White, Zelano, & Branigan, P.C.

[57] ABSTRACT

Novel triiodo 5-aminoisophthaldiamides are provided, where the amino and one of the amide nitrogens are substituted. The compounds have at least two hydroxyl groups and are found to provide low viscosity and osmolality. Procedures for preparing the compounds are provided.

24 Claims, No Drawings

CARBOXAMIDE NON-IONIC CONTRAST MEDIA

CROSS-REFERENCE TO RELATED APPLICATIONS

This application is a continuation-in-part of application Ser. No. 08/365,185, (now abandoned) filed Dec. 28, 1994, which is a continuation of application Ser. No. 07/548,416, filed Jul. 5, 1990 (now abandoned), which is a continuation-in-part of application Ser. No. 431,527, filed Nov. 3, 1989 (now abandoned) which is a CIP of application Ser. No. 375,714, filed Jul. 5, 1989, (now abandoned), both of which are entirely incorporated by reference herein.

INTRODUCTION

1. Technical Field

The field of the invention is methods of preparation and compositions for use as non-ionic contrast media.

2. Background

Radiographic contrast media for visualization of the cardiovascular system and body cavities must have low viscosity, be highly water soluble, non-toxic, and have a high iodine content. Low viscosity is imperative for rapid delivery, to momentarily replace rapidly flowing blood, such as in cardioangiography or high dose urography, or contrast enhancement in computerized tomography. To be non-toxic, the compound must be highly hydrophilic, non-ionic, and of osmolality close to the body milieu. While the non-ionic monomeric media of the prior art have a reasonable biological tolerance and useful viscosity, they are hyperosmolal vis-a-vis the body milieu. Typically, at the diagnostically useful concentration of 300 mg I/ml, they substantially exceed the physiological value of 310 mOsm. Hyperosmolality of these solutions necessarily drives water out of cells, disrupting the cellular membranes, perturbing the overall electrolytic balance, and damaging the lining of vessels or of organ cavities. Also, hyperosmolality has been shown to be one cause of vascular pain invariably elicited by hyperosmolal contrast media.

Most of the non-ionic contrast media, whether monomeric or oligomeric, are aromatic amides, with one or more polyhydroxy, lower aliphatic alkyl, and acyl subgroups bonded to nitrogen, with annular carboxamides and amino groups. The triiodinated benzene ring contains a number of functionalities in close spatial relationships. The prior art describes several hydroxyalkylamines attached as amides. Examples of these amines include: serinol; 1-amino-2,3-propanediol; N-methyl 1-amino-2,3-propanediol; aminotetritols; ethanolamine, diethanolamine, or tromethamine.

Substitution of the carboxyl groups in the 1 and 3 positions with the same hydroxyalkylamine poses a severe limitation on the design, since the substitutents practically available are either too small to solubilize the molecule, or too large to result in a solution of low viscosity (Nycomed, U.S. Pat. Nos. 4,021,481 and 3,701,771; Schering AG, U.S. Pat. No. 4,547,357, Bracco, U.S. Pat. No. 4,001,323). For this reason, improved compounds were developed where the two hydroxyalkylamines were different (Schering AG U.S. Pat. No. 4,364,921). Such compounds, however, have a complex synthesis and are costly to synthesize.

Relevant Literature

U.S. Pat. Nos. 3,701,771, 4,001,323, 4,021,481, 4,364,921, 4,547,357 and co-pending U.S. application Ser. No. 214,663, filed Jul. 1, 1988 (now U.S. Pat. No. 4,954,348) are illustrative of various compounds reported as useful for non-ionic contrast media.

SUMMARY OF THE INVENTION

Non-ionic contrast media are provided based on an asymmetrical triiodoisophthalic diamide, where the remaining ring position is occupied by a substituted nitrogen, one of the carboxyl groups being unsubstituted amide, and the other carboxyl groups being at least a mono-(hydroxyalkyl) substituted amide. The molecule has at least two hydroxyl groups.

DESCRIPTION OF SPECIFIC EMBODIMENTS

Non-ionic contrast media are provided based on an acylamido substituted triiodoisophthalic diamide, where only one of the amide nitrogens is at least monosubstituted. The compounds may be inexpensively synthesized in good yield and obtained in high purity. The subject compounds have been found to provide low osmolality, while at the same time maintaining moderate to low viscosity.

The compounds of the subject invention will for the most part have the following Formula (I):

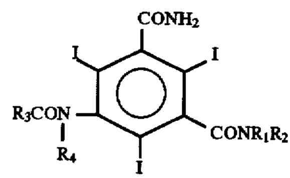

I wherein:

$R_1$ is hydrogen, lower alkyl or hydroxyalkyl, wherein said alkyl group is from 1 to 3, usually 1 to 2 carbon atoms, and said hydroxyalkyl group has at least 0.5 hydroxyls per carbon atom and up to n−1 hydroxyl groups, where n is the number of carbon atoms, hydroxyalkyl being of from 2 to 6, usually 2 to 4 carbon atoms;

$R_2$ is a mono- or polyhydroxyalkyl, of from 2 to 6, usually 2 to 4 carbon atoms, having at least one hydroxyl group and not less than n−2 and not more than n−1 hydroxyl groups, where n is the number of carbon atoms;

$R_3$ is lower alkyl, hydroxy (lower alkyl), or lower alkoxy (lower alkyl), where alkyl is of from 1 to 4 carbon atoms, usually of from 1 to 3 carbon atoms, and alkoxyl is of from 1 to 3, usually 1 to 2, carbon atoms, with the number of oxy groups varying from 0 to n−1, where n is the number of carbon atoms, or two $R_3$ groups may be taken together to define a bridge of from 0 to 2 carbon atoms, preferably 1 carbon atom;

$R_4$ is hydrogen, lower alkyl, or mono- or polyhydroxyalkyl, where the alkyl groups and the hydroxyl groups come within the definitions as described above for analogous groups.

The alkyl groups may be straight chain or branched, usually straight chained where carbon atoms will normally be other than quaternary.

The alkyl residue in the mono- or polyhydroxyalkyl $R_1$ and $R_2$ will usually have 2 to 6 carbon atoms, usually 2 to 4 carbon atoms. Preferably, the groups will have 1 to 5, usually 1 to 3 hydroxy groups. These hydroxy groups may be primary, secondary, or tertiary. Examples include trishydroxymethylmethyl, hydroxyethyl, dihydroxypropyl, and trihydroxybutyl. Carbamides may be prepared using 3-amino-1,2-propanediol, serinol or amino-tetritols, i.e., threitol and erythritol, either in D,L mixture or optically pure forms, ethanolamine, or diethanolamine, or tromethamine, or derivatives thereof, where the hydroxyl groups are reversibly protected. $R_1$ is hydrogen, or lower alkyl, preferably hydrogen or methyl. $R_3$ is a lower alkyl or oxyalkyl of 1 to 6, usually 1 to 4 carbon atoms, preferably methyl, hydroxymethyl or hydroxyethyl. Also exemplified are alkoxyalkyls containing alkoxyl groups of 1 to 3 carbon atoms, preferably 1 to 2 carbon atoms, and alkyls of from 1 to 3 carbon atoms, more particularly methoxymethyl. Alternatively, two $R_3$ groups are taken together to be a bond, methylene or ethylene, particularly methylene. $R_4$ is hydrogen, alkyl or mono- or polyhydroxyalkyl of from 1 to 6, usually 1 to 4, carbon atoms, including methyl, ethyl, propyl, hydroxyethyl, and dihydroxypropyl.

Monomeric compounds of interest include 5-[N-(2-hydroxyethyl)methoxyacetamido]-2,4,6-triiodo-3-[N-(1,3,4-trihydroxybut-2-yl)]carbamoyl benzamide; 5-[N-(2-hydroxyethyl)hydroxyacetamido]-2,4,6-triiodo-3-[N-(2,3-dihydroxypropyl)]carbamoyl benzamide; 5-[N-(2,3-dihydroxypropyl)acetamido]-2,4,6-triiodo-3-[N-(2,3-dihydroxypropyl)]carbamoyl benzamide; 5-[N-(2,3-dihydroxypropyl)glycolamido]-2,4,6-triiodo-3-[N-(2-hydroxyethyl)]carbamoyl benzamide; 5-[N-(1,3,4-trihydroxy-but-2-yl)acetamido]-2,4,6-triiodo-3-[N-(2-hydroxyethyl)]carbamoyl benzamide; 5-[N-(methyl) glycolamido]-2,4,6-triiodo-3-[N-(1,3,4-trihydroxy-erythro-but-2-yl]carbamoyl benzamide; and 5-[N-(2-hydroxyethyl) acetamido]-2,4,6-triiodo-3-[N-(1,3,4-trihydroxythreobut-2-yl)]carbamoyl benzamide.

Dimeric compounds of interest include malonic acid bis-[{3-N-(2,3-dihydroxypropyl-carbamoyl)5-carbamoyl}-2,4,6-triiodo-N-(2,3-dihydroxypropyl)anilide; malonic acid bis-[{3-N-(2,3-dihydroxypropyl-carbamoyl)5-carbamoyl}-2,4,6-triiodo-N-(2-hydroxyethyl)]anilide; and malonic acid bis-[{3-N(1,3,4-trihydroxy-but-2-yl-carbamoyl)5-carbamoyl}-2,4,6-triiodo-N-methyl]anilide.

The compositions of the subject invention will have from about 50 to 52% iodine, usually about 51%, have a viscosity of a solution of 300 mg I/ml at 37° C. (cps) in the range of about 4 to 5, and an osmolality of 300 mg I/ml at 37° C. in mOsm for an aqueous solution in the range of about 275 to 400, more usually about 285 to 375, while with a pharmaceutical formulation, it will range from about 300 to 400, more usually about 325 to about 390.

The subject compositions are formulated in accordance with conventional conditions. Usually, the formulations will comprise an aqueous medium, which includes a physiologically acceptable chelated calcium salt, e.g., EDTA, a buffer to provide a pH in the range of about 6.5 to 7.5, particularly about 7, where the buffer may include tris, carbonate, citrate, or combinations thereof. Other additives which may be included are bicarbonate, phosphate, etc. The chelated calcium will generally be present in from about 5 to 15, usually about 10 mg/100 ml, while the buffer will generally be present in the amount from about 2 to 10 mM.

Conventional reactions may be combined in a defined pathway to prepare the subject compounds. Thus, in a subject process, the products of this invention can be prepared, for example, from the compound of Formula (II):

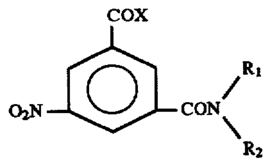

where $R_1$ and $R_2$ are as defined previously, and X is either a lower alkyl ester or a halogen. Compounds under general Formula (II) are prepared by reacting an hydroxyalkylamine ($NHR_1,R_2$) whose OH groups are protected or unprotected, with a commercially available monoester of 5-nitroisophthalic acid, followed by activation of the remaining carboxyl group. Such activation is suitably achieved when X is a halogen such as Cl, Br, I, or alkoxy with chlorine and methoxy being preferred.

The ester group of 5-nitroisophthalic acid, mono-ester is aminolyzed with the hydroxyalkylamine of general formula $HNR_1R_2$ as defined above, or aminolysis can be achieved with ammonia first. The remaining carboxyl group is then activated as described above. If the hydroxyl groups of the residue $NR_1R_2$ are unprotected and could be affected by the activation, they can suitably be protected by conventional means such as O-acetylation or by isopropylidination.

The compound of general Formula (II) can be conveniently crystallized from water or lower alcohols.

After reaction with anhydrous ammonia or ammonium hydroxide, where the asymmetrical isophthaldiamide is obtained, the compound is hydrogenated, triiodinated and acylated in a conventional manner to arrive at general Formula (III):

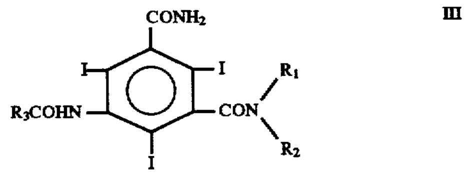

where $R_1$, $R_2$, and $R_3$ are defined as above.

Reduction and iodination is typically carried out by standard methods using as catalysts, palladium on carbon or Raney nickel in water or lower alcohols, and hydrogen under low or high pressure. The resulting 5-aminoisophthalic acid bisamide is then iodinated by known methods. The compound is then conveniently recovered as it crystallizes from the reaction mixture, washed, dried, and subjected to acylation, also following known methods. Thus, an activated acyl $R_3CO—X$, where X is halo or the same acyl group to form an anhydride, and catalyzing solvents such as pyridine, DMA, or DMF may be used.

If compounds according to Formula (I), where $R_4$ is other than hydrogen, are prepared, the alkylation is carried out by standard methods. Except for lower alkyls which are conveniently introduced at an earlier stage of the synthesis, the reaction with hydroxyalkyl residues is carried out typically as the last step. Such an alkylation can be carried out in a high boiling glycol solvent, such as ethylene or propylene glycol, and highly basic pH achieved with sodium methoxide, sodium hydroxide, or other inorganic or organic bases.

Alternatively, it is sometimes advantageous for the purposes of purification where side products are formed which would otherwise be difficult to remove, by conventional purification methods, to maintain the presence of one carboxyl group until the latter stages of the reaction sequence, so that the compound can conveniently be dissolved in water as a salt and thereafter precipitated or reprecipitated with an inorganic acid. Preferred salts include ammonium, sodium, potassium, calcium, barium or lithium.

Such alternative process is based on the reduction, iodination and acetylation of compounds of Formula (II) (where X=OH) in the manner described above to arrive at Formula (IV):

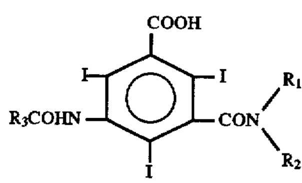

IV where $R_1$, $R_2$ and $R_3$ are defined above.

The hydroxyl groups are protected prior to activation of the carboxyl group. It is also necessary to diacylate the anilide with $R_3CO$, as this nitrogen would likewise be adversely affected during carboxyl activation. The carboxyl group will be activated as described above, with the acid chloride being preferred, although mixed anhydrides may be used, e.g., t-butyloxycarbonyl. Compounds under Formula (IV) can conveniently be crystallized from an aprotic solvent and reacted with ammonium hydroxide or ammonia, followed by alkylation as the last step.

Effective amidation usually requires use of either an excess of amidating base as an acid acceptor or alternatively, tertiary amines, such as triethylamine, tributylamine, pyridine, or inorganic bases such as bicarbonate or carbonate.

Yet another variation of the synthetic process can be applied when undesirable side products occur. Thus, alkylation of the anilide may be carried out prior to the amidation. Alkylation of the compounds under general Formula (IV), where $R_1$, $R_2$, and $R_3$ are as defined above may be carried out by known methods as described above.

During alkylation to introduce $R_4$, the protecting groups $R_3CO$ are lost, and thus the hydroxyl groups of $R_1$ and $R_2$ (also $R_4$ if present) must be re-protected prior to carboxyl activation and subsequent amidation with ammonia. Acetyl groups are most often employed for this purpose.

Following the final step, if hydroxyl groups are still protected, such as would be the case when alkylation is not carried out as the last step, the protecting groups may conveniently be removed by standard means such as exposure to ion exchange resins, or use of acids or bases in catalytic amounts in alcoholic or aqueous solvents.

Desalting can be accomplished by known methods. Typically, salts will be removed by ion exchange resins, either mixed-bed or in separate columns individually containing an anionic or cationic exchange resin. Alternatively, the compounds of general Formula (I) can be absorbed on a polystyrene-absorbing neutral resin and thereafter eluted.

Following removal of the salts, the product can now be crystallized from a variety of solvents, preferably lower alcohols. Decolorization is achieved by refluxing in aqueous solution with activated charcoal.

The dimer is conveniently prepared from the benzamide, with the amino nitrogen alkylated and the remaining carbonyl group activated, e.g., chlorocarbonyl. The dibasic acid is used in activated form, particularly as the diacyl dichloride in an organic aprotic polar solvent. The ring carbon bound chlorocarbonyl is then hydroxyalkylamidated to obtain the final product.

The compounds of this invention and under general Formula (I) are stable in aqueous solutions; they readily form supersaturated solutions which also remain stable. The solutions can be autoclaved by standard means. At diagnostically useful iodine concentrations, the compounds have osmolalities which typically are very close to the physiological values. At the same time, the solution viscosity is low. Thus, the objective of this invention to overcome the previously recognized mutual exclusivity of the two factors, i.e., low osmolality and low viscosity, has been accomplished. As a result, the novel compounds have excellent local and systemic tolerance. The compounds have good biological tolerance and high iodine content, particularly as compared to presently available non-ionic radiographic contrast media.

As examples of the properties of the benzamide class compounds, data were generated for the compounds (11) (Claim 5) and (19) (Claim 6). For comparison, data on prior art compounds are also shown in Table I.

TABLE 1

| | | | | | Intravenous Toxicity Approximate ranges | | |
|---|---|---|---|---|---|---|---|
| | | Viscosity of | Osmolality of 300 mg I/ml Solutions | | i.v. $LD_{50}$ (g I/kg) (10 day interval) | | |
| | % Iodine of Molecular Weight | 300 mg I/ml at 37° C. (cps) | Aqueous Solution (mOsm) | Pharmaceutically Formulated Sol'n (mOsm) | Male mouse 16–20 g Body Weight | Male Rat 80–100 g Body Weight | % Iodide released from compound by 20' autoclaving (w/w) |
| Iohexol | 46 | 6.3* | 650 | 685 | 16–17 | 11.5–12.5 | 0.004 |
| Iopamidol | 49 | 4.7* | 671 | 704 | 16–18 | 12–13 | 0.004 |
| Iopromide | 48 | 4.6* | 607 | 630 | 14–16 | 11–12 | 0.004 |
| Ioxilan | 48 | 4.7 | 560 | 588 | 16–18 | 12–13 | <0.001 |
| Compound 19 (BP-8) | 51 | 4.1 | 365 | 390 | 14–16 | 13–14 | 0.003 |
| Compound 11 (BP-6) | 51 | 4.2 | 300 | 326 | 15.5–16.5 | 15.5–17.5 | 0.003 |
| Compound 41 (BP-12) | 52 | 3.5 | 314 | 322 | 16–17.5 | 15–17 | <0.001 |

*Reported; all other data were generated in our laboratory using pharmaceutically formulated compounds except where stated.

The observed low osmolality and concurrent low toxicity was only previously achieved in non-ionic dimers, which, however, cannot be utilized in general uroangiography due to their high viscosity which, for a comparable solution concentration, is at least two times higher.

The novel compounds show an excellent general biological tolerance. Since high osmolality is the causative factor of vascular pain and a major side effect of depicting the peripheral limb vasculature (Sovak, M., Current Contrast Media and Ioxilan, Comparative Evaluation of Vascular Pain by Aversion Conditioning, Investigative Radiology, September, 1988 Supp). This is one of the major diagnostic procedures in vascular radiology. The novel compounds of this invention are expected to be virtually painless in such procedures. Because of their physiochemical and pharmacological properties, the novel compounds are suitable as water-soluble contrast media for the visualization of the urine excretory and cardiovascular systems, and body cavities and for general contrast enhancement in computerized tomography. The injectable solutions of the novel compounds can be prepared by dissolution in water and adding standard physiological-compatible buffers, and stabilizers such as chelating agents. The compounds also are suitable for enteral application when formulated with carriers usually employed in the pharmacopoeias. The dimers find particular use for myelograms.

For intravascular use, the compounds of this invention contain 20%–80% weight by volume, with iodine conentrations of 150 to 400 mg/ml preferred.

The following examples are offered by way of illustration and not by way of limitation.

EXPERIMENTAL

EXAMPLE 1

Amidation of 5-nitroisophthalic acid, monomethyl ester (1) with (threo)-2-amino-1,3,4-butanetriol into: 5-nitro-3{N-(1,3,4-trihydroxy-threo-but-2-yl) }carbamoyl benzoic acid (2)

The starting material (1, 22.5 g, 0.1 mole) was mixed with (threo)-2-amino-1,3,4-butanetriol (30.25 g, 0.25 moles) and the suspension heated to 110°–120° C. for 30 min. Complete conversion to the product was seen by TLC and the solution was poured into 1N hydrochloric acid (200 ml) to precipitate the product. After cooling overnight, the product was filtered and washed with ice-cold water (20 ml×2). Drying in vacuo gave a white solid (2, 21.0 g, 67% yield).

EXAMPLE 2

Esterification of 5-nitro-3{N-(1,3,4-trihydroxy-threo-but-2-yl)}carbamoyl benzoic acid (2) with dimethyl sulfate into: methyl 5-nitro-3{N-(1,3,4-trihydroxy-threo-but-2-yl)}carbamoyl benzoate (3)

The title compound (2, 15.7 g, 0.05 moles) was dissolved in 1N sodium hydroxide solution (55 ml) and the solution cooled to <20° C. Dimethylsulfate (9.45 g, 0.075 moles) was added over 5 min and the pH was maintained between 8–10 by the occasional addition of 5N sodium hydroxide solution. The solution was stirred for ca. 12 hr at room temperature after which the insoluble solid was filtered off. The pasty solid was washed with cold water (50 ml×2) and was dried in vacuo to give a powder (3, 11.8 g, 72% yield).

EXAMPLE 3

Amidation of methyl 5-nitro-3-{N-(1,3,4-trihydroxy-threo-but-2-yl)}carbamoyl benzoate (3) with ammonia into: 5-nitro-3-{N-(1,3,4-trihydroxy-threo-but-2-yl)}carbamoyl benzamide (4)

The ester (3, 10.0 g, 0.0305 moles) was dissolved in methanol (50 ml) and concentrated ammonium hydroxide (20 ml, ca. 0.3 moles) was added. The suspension was heated in a sealed vessel at 50°–60° C. for 30 min when TLC indicated reaction completion. The methanol and ammonium hydroxide were removed by distillation, and were replaced by $H_2O$ (50 ml). The mixture was cooled overnight, after which the insoluble product was filtered, and washed with cold water (5 ml×2). Vacuum drying gave the white mixed amide (4, 7.15 g, 75% yield).

EXAMPLE 4

Chlorination of 5-nitroisophthalic acid, monomethyl ester (1) with thionyl chloride into: 5-nitroisophthalic acid, monomethyl ester, monoacid chloride (5)

The title compound (1, 225 g, 1 mole) was dissolved in ethyl acetate (0.5 L) and N,N-dimethylformamide (0.1 ml) added as a catalyst. The solution was heated to 70° C. and thionyl chloride (219 ml, 3 moles) added over 1.25 hr. The temperature was subsequently maintained at 70° C. for 2 hr.

The thionyl chloride was codistilled with ethyl acetate (200 ml×3) and the product dissolved in hot ethyl acetate (250 ml) and precipitated with cyclohexane (1 L), filtered, and washed with cyclohexane (200 ml×2). Drying at 50° C. under vacuum gave a white solid (5, 216 g, 89% yield).

EXAMPLE 5

Amidation of 5-nitroisophthalic acid, monomethyl ester mono acid chloride (5) with aminodioxepan into: methyl 5-nitro-3-{N-(trans-2,2-dimethyl-6-hydroxy-1,3-dioxepan-5-yl)}carbamoyl benzoate (6)

The monoester, monochloride (5, 100 g, 0.411 moles) was dissolved in dry tetrahydrofuran (1 L) and the solid aminodioxepan (132.8 g, 0.825 moles) was added in portions over 15 min, keeping the temperature below 25° C. with the aid of an ice bath. Thereafter, the hererogenous mixture was allowed to stir for 30 min at room temperature, when TLC showed reaction completion.

The insoluble amine hydrochloride was filtered off and the tetrahydrofuran was removed from the filtrate by distillation. The residue was dissolved in ethyl acetate (400 ml) near the boiling point, and the solution allowed to stand for several days until crystallization of the product was complete. The solid was filtered off, washed with cold ethyl acetate (50 ml×2) and dried in a vacuum oven, giving an off-white product (6, 82.4 g, 55% yield).

EXAMPLE 6

Amidation of methyl 5-nitro-3-{N-(trans-2,2-dimethyl-6-hydroxy-1,3-dioxepan-5-yl)}carbamoyl benzoate (6) with ammonium hydroxide into: 5-nitro-3-{N-(trans-2,2-dimethyl-6-hydroxy-1,3-dioxepan-5-yl)}carbamoyl benzamide (7)

A Parr pressure reactor (800 ml) was charged with the title compound (6, 80 g, 0.22 moles), methanol (110 ml) and 15N ammonium hydroxide (225 ml, 3.38 moles). The reaction vessel was sealed and submerged in a water bath at 50° C. for 2 hr, when TLC indicated complete reaction. The heterogeneous reaction mixture was mixed with $H_2O$ (100 ml) and then stripped to a foam. The foam was slurried in $H_2O$ (100 ml), filtered and washed two times with 50 ml $H_2O$ to obtain a white solid (7, 60.4 g, 79% yield).

EXAMPLE 7

Reduction and deprotection of 5-nitro-3-{N-(trans-2,2-dimethyl-6-hydroxy-1,3-dioxepan-5-yl) }carbamoyl benzamide (7) with hydrogen and palladium on carbon and hydrochloric acid into: 5-amino-(hydrochloride)-3-{N-(1,3,4-trihydroxy-threo-but-2-yl)}carbamoyl benzamide (8)

A Parr pressure reactor (2.0 L) was charged with the title compound (7, 58 g, 0.16 moles), 1N hydrochloric acid (410 ml) and palladium-on-carbon (10% Pd/C, 5.8 g, 1% Pd w/w). The reaction vessel was connected to a hydrogenator and shaken under 50 psi hydrogen gas for 2 hr, when HPLC indicated conversion to product (8). The palladium catalyst was filtered and the acetone formed during deprotection was removed in vacuo at 50° C. The resulting clear solution (8, 450 ml, 90% yield) was taken directly to iodination.

EXAMPLE 8

Iodination of 5-amino-(hydrochloride)-3-{N-(1,3,4-trihydroxy-threo-but-2-yl)}carbamoyl benzamide (8) with iodine monochloride into: 5-amino-2,4,6-triiodo-3-{N-(1,3,4-trihydroxy-threo-but-2-yl)}carbamoyl benzamide (9)

The title compound (8, 0.14 moles) in 1N hydrochloric acid (450 ml) was heated to 85° C. and iodine monochloride (135 ml, 0.49 moles) was added. The reaction mixture was heated at 85° C. for 2 hr, when HPLC indicated that the reaction was done. The reaction mixture was cooled to 25° C. and extracted 2×cyclohexene (200 ml), 3×dichloromethane (300 ml), and 5×chloroform (200 ml) until all the purple color was removed from the aqueous layer. The resulting light yellow solution was recirculated on a column containing Duolite-A340 (800 g) and Dowex 50W-X8 (266 g) resins. The resins were flushed with $H_2O$ (6 L) and the solution was concentrated to 300 ml when a white crystalline solid began crystallizing. The product was filtered to obtain a white solid (9, 40 g, 0.06 moles, 43% yield).

EXAMPLE 9

Acetylation of 5-amino-2,4,6-triiodo-3-{N (1,3,4-trihydroxy-threo-but-2-yl)}carbamoyl benzamide (9) with acetic anhydride into: 5-diacetylamino-2,4,6-triiodo-3-{N-(1,3,4-triacetoxy-threo-but-2-yl)}carbamoyl benzamide (10)

The title compound (9, 90 g, 0.14 moles) was mixed with acetic anhydride (500 ml, 4.95 moles) at 70° C., with vigorous stirring. Perchloric acid (0.36 ml, 0.004 moles) catalyst was added, causing the temperature to rise to 85° C. The reaction mixture was stirred at 85° C. for 1 hr, when it became homogenous and TLC indicated reaction completion. Sodium acetate (0.33 g, 0.004 moles) was added to neutralize the perchloric acid, and the solvent was removed to obtain a thick brown oil. The oil was diluted with butyl acetate (200 ml) at 70° C., followed by solvent removal. The stripping procedure was repeated two times to obtain a brown foam (10, 113 g, 0.13 moles, 93% yield).

EXAMPLE 10

Deacetylation and alkylation of 5-diacetylamino-2,4,6-triiodo-3{N-(1,3,4-triacetoxy-threo-but-2-yl)}carbamoyl benzamide (10) with sodium methoxide and 2-chloroethanol into: 5-{N-(2-hydroxyethylacetamido)}-2,4,6-triiodo-3-{N-(1,3,4-trihydroxy-threo-but-2-yl)}carbamoyl benzamide (11)

The title compound (10, 113 g, 0.13 moles) was dissolved in methanol (500 ml) to which was added 25% sodium methoxide (55 g, 0.25 moles) at 50° C. After 5 hr, HPLC indicated the deacetylation was complete and the solution was neutralized with Dowex 50 W-X4 resin (10 g). The resin was filtered and the filtrate was concentrated to 400 ml. The neutral methanolic solution was warmed to 45° C. and charged with trisodium phosphate dodecahydrate (129 g, 0.34 moles) and 2-chloroethanol (18.2 ml, 0.272 moles). The reaction was stirred at 45° C. for 48 hr, when chloroethanol (4.7 ml, 0.07 moles) and sodium methoxide (14.7 g, 0.07 moles) was added. After 71 hr, HPLC indicated the reaction had gone to completion. The insoluble salts (89 g) were removed by filtration and the solution neutralized with hydroxhloric acid (6N, 7 ml). The solution was concentrated to obtain a brown foam (11) (94 g, 0.12 moles, 92% yield).

EXAMPLE 11

Amidation of 5-nitroisophthalic acid, monomethyl ester (1) with 3-amino-1,2-propanediol into: 5-nitro-3-{N-(2,3-dihydroxpropyl)}carbamoyl benzoic acid (12)

The starting material (1, 225 g, 1 mole) was mixed with 3-amino-1,2-propanediol (227.8 g, 2.5 moles) and the heterogeneous mixture was heated to 110°120° C. for 1 hr. At this point, the reaction was complete, and the homogeneous mixture was mixed with water (1 L), and concentrated HCl (170 ml). The mixture was cooled for several days to fully precipitate the product, and the solid was filtered off and washed with cold water (50 ml×2). Vacuum drying gave a white solid (12, 193 g, 68% yield).

EXAMPLE 12

Reduction of 5-nitro-3-{N-(2,3-dihydroxy-propyl)}carbamoyl benzoic acid (12) with hydrogen and palladium-on-carbon into: 5-amino-(hydrochloride)-3-{N-(2,3-dihydroxypropyl)}carbamoyl benzoic acid (13)

The nitro acid (12, 180 g, 0.634 moles) was mixed with water (1 L), and concentrated HCl (60 ml) and 10% palladium-on-carbon (18 g) were added. The suspension was hydrogenated at 2–4 atmospheres until the pressure remained constant, by which time HPLC and TLC indicated reaction completion. The palladium-on-carbon was removed by filtration and the homogeneous solution was used without product isolation for the following reaction (13, approximate yield 98%).

EXAMPLE 13

Iodination of 5-amino-(hydrochloride)-3-{N-(2,3-dihydroxypropyl)}carbamoyl benzoic acid (13) with iodine monochloride into: 5-amino-2,4,6-triiodo-3-{N-(2,3-dihydroxy-propyl)}carbamoyl benzoic acid (14)

The title compound (13, ca. 0.62 moles in 1.5 L water) was further diluted with water to a total volume of 4 L and heated to 85° C. Over 20 minutes, iodine monochloride (4.1 molar, 499 ml, 2.05 moles) was added and the temperature maintained at 90° C. for 6–8 hr. HPLC indicated reaction completion. The homogeneous mixture was cooled, extracted with 1,2-dichloroethane:cyclohexene (9:1, 500 ml×1), followed by 1,2-dichloroethane (250 ml×2). The aqueous layer was then concentrated by distillation to 0.9 L, and cooled for several days to complete the precipitation of the solid. Filtration, washing with cold water (100 ml×2) and vacuum drying gave the tan product (14, 286 g, 73% yield).

EXAMPLE 14

Acetylation of 5-amino-2,4,6-triiodo-3-{N-(2,3-dihydroxypropyl)}carbamoyl benzoic acid (14) with acetic anhydride into: 5-diacetylamino-2,4,6-triiodo-3-{N-(2,3-diacetoxpropyl)}carbamoyl benzoic acid (15)

The starting material (14, 100 g, 0.158 moles) was mixed with acetic anhydride (300 ml, 3.16 moles) and 70% perchloric acid (0.2 ml), and heated to 80°–90° C. for 8 hr. The mixture was neutralized with anhydrous sodium acetate (0.25 g) and the acetic anhydride and acetic acid removed by distillation at 70°–80° C. The oily residue was azeotroped with butyl acetate (100 ml×2), then dissolved in ethyl acetate (250 ml), and taken directly into chlorination (15, approximate yield 90%).

EXAMPLE 15

Chlorination of 5-diacetylamino-2,4,6-triiodo-3-{N-(2,3-diacetoxypropyl)}carbamoyl benzoic acid (15) with thionyl chloride into: 5-diacetylamino-2,4,6-triiodo-3-{N-(2,3-diacetoxyropyl)}carbamoyl benzoyl chloride (16)

To the starting material (15, ca. 0.142 moles) in ethyl acetate (225 ml) was added thionyl chloride (57 ml, 0.78 moles) at 65°–70° C., and the temperature increased afterwards to 75°–80° C. for 1 hr. Thionyl chloride and ethyl acetate were vacuum distilled. The residue was azeotroped with butyl acetate (100 ml>2), and vacuum dried. The brown foam (16, ca. 130 g, estimated yield 95%) was taken directly into the subsequent amidation step.

EXAMPLE 16

Amidation of 5-diacetylamino-2,4,6-triiodo-3-{N-(2,3-diacetoxypropyl)}carbamoyl benzoyl chloride (16) with ammonia into: 5-acetylamino-2,4,6-triiodo-3-{N-(2,3-diacetoxypropyl)}carbamoyl benzamide (17)

The acid chloride (16, ca. 0.135 moles), was dissolved in dry N,N-dimethylacetamide (150 ml). This solution was cooled to 0°–5° C., anhydrous ammonia (ca. 20 ml) was condensed into the mixture using a dry ice/acetone condenser and the reaction mixture was kept sealed at room temperature for 24 hr. The ammonia and DMA were removed by vacuum distillation. 1-pentanol (500 ml) precipitated a solid which was filtered and washed with 1-pentanol (150 ml×2). Vacuum drying gave a tan solid (17, 82 g, 80.2% yield).

EXAMPLE 17

Deacetylation of 5-acetylamino-2,4,6-triiodo-3-{N-(2,3-diacetoxypropyl)}carbamoyl benzamide (17) into: 5-acetylamino-2,4,6-triiodo-3-{N-(2,3-dihydroxypropyl)}carbamoyl benzamide (18)

The title compound (17, 81.2 g, 0.107 moles) was suspended in water (203 ml) and then treated with the dropwise addition of 50% w/w sodium hydroxide in water (16.9 ml, 0.322 moles). With stirring, total solution was obtained. The solution was degassed under vacuum for 30 min at which time 12M HCl (15 ml, 0.18 moles) was added. After storage at 4° C., the resulting precipitated solid was filtered, washed with ice water (3×50 ml), ethanol (80 ml), and vacuum dried to the product (18, 54.1 g, 75% yield).

EXAMPLE 18

Alkylation of 5-acetylamino-2,4,6-triiodo-3-{N-(2,3-dihydroxypropyl)}carbamoyl benzamide (18) into: 5-{N-(2,3-dihydroxypropyl)acetamido}-2,4,6-triiodo-3-{N-(2,3-dihdroxypropyl)}carbamoyl benzamide (19)

The title compound (18), 39.7 g, 0.059 moles) was dissolved in propylene glycol (16.7 ml), ethanol (120 ml), and 25% w/w sodium methoxide (17.6 ml, 0.077 moles). Chloropropanediol (9.78 g, 0.0885 moles) was added and the mixture was stirred at 25° C. for 1 hr. The reaction was warmed to 33° C. and stirred for another 19 hr during which time 25% w/w sodium methoxide (3.4 ml, 0.015 moles) was added. The reaction was quenched with 12M HCl, distilled under vacuum, reconstituted with $H_2O$ (200 ml), and distrilled again to give an aqueous solution that was deionized with Dowex 50 $H^+$ resin (62 g) and Duolite A-340 $OH^-$ resin (140 g). Elution of the resins with $H_2O$ and concentration gave a 150 g solution that was treated with Norit Ultra SX charcoal (1.00 g) at 60° C. for 14 hr. The charcoal was filtered giving an aqueous solution that was stirred for 2 hr with Dowex 50 $H^+$ (1.0 g) and Duolite A-340 $OH^-$ (4 g). The resin was filtered and the aqueous solution was distilled to 50.3 g of an oil containing the product (19, 32.8 g, 74% yield) in a glycerol/propylene glycol base. This oil was purified as described in the following step.

EXAMPLE19

Peracetylation, silica column purification, and subsequent deacetylation of: 5-{N-(2,3-dihdroxroxpropyl)acetamido}-2,4,6-triiodo-3-{N-(2,3-dihydroxypropyl)}-carbamoyl benzamide (19)

The title compound (19, 16.4 g, 0.022 moles) dissolved in glycerol/propylene glycol oil (total mass, 25.15 g) was diluted with pyridine (1.74 g, 0.022 moles) and acetic anhydride (115 g, 1.12 moles), and then warmed to 60° C. for 18 hr. The reaction was distilled under reduced pressure to an oil, dissolved in $CHCl_3$ (100 ml) and extracted with 0.1N HCl (2×50 ml) and 15% w/v brine (2×50 ml). The $CHCl_3$ layer was dried over $MgSO_4$, filtered, and distilled to an oil. This oil was purified on a 900 g silica column utilizing a solvent gradient which ran from 5% acetic acid, 95% chloroform to 5% acetic acid, 4% methanol, 91% chloroform. Purified fractions were combined, distilled to a foam, and then treated with methanol (30 ml) and 25% w/w sodium methoxide in methanol (0.98 g, 0.0054 moles). After 30 min, the solution was distilled, reconstituted with methanol (20 ml), and then stirred with Dowex 50 $H^+$ resin (1.3 g). After the pH decreased from 12 to 5, the resin was filtered off, giving a solution that was distilled to a foam, reconstituted with $H_2O$ (25 ml), and evaporated to the solid title compound (19, 8.12 g, 49% yield).

EXAMPLE 20

Deacetylation of 5-diacetylamino-2,4,6-triiodo-3-{N-(2,3-diacetoxypropyl)}carbamoyl-benzoic acid (15) into: 5-acetylamino 2,4,6-triiodo-3-{N-(2,3-dihydroxpropyl)}carbamoyl benzoic acid (20)

The title compound (15, 720 g, 0.9 moles) was dissolved in 500 ml methanol, and 25% w/w sodium methoxide in methanol (345 ml, 1.5 moles) was added. After 4 hr at 45°–50° C. the reaction was distilled under reduced pressure, acidified with 12M HCl (124 ml, 1.5 moles), and the salts filtered off. The filtrate was distilled under reduced pressure to give an oil which was diluted with n-propanol (680 ml). After crystallizing at 4° C., the resulting solid product (20) was filtered off, washed with n-propanol (2×300 ml), and dried in vacuo. Yield was 391 g (64%).

EXAMPLE 21

Alkylation of 5-acetylamino-2,4,6-triiodo-3-{N-(2,3-dihydroxypropyl)}carbamoyl benzoic acid (20) into: 5-{N-(2,3-dihydroxypropyl)acetamido}-2,4,6-triiodo-3-{N-)2,3-dihydroxypropyl)}carbamoyl benzoic acid, sodium salt (21)

The title compound (20, 100 g, 0.148 moles) was dissolved in 400 ml methanol. Solid $Na_3PO_4.12\ H_2O$ (140.6 g, 0.37 moles) was added, followed by chloropropanediol (32.7 g, 0.296 moles) and 25% w/w sodium methoxide in methanol (24.1 g, 0.111 moles), added dropwise. The reaction mixture was warmed to 40° C. for 10 hr during which more 25% sodium methoxide (8.0 g, 0.0368 moles) was added in portions. Salts were filtered off and the methanol filtrate was acidified with 12M HCl (3.5 ml), rotavaped to a thick oily product (21) and carried directly into the next reaction.

EXAMPLE 22

Acetylation of the sodium salt of 5-{N-(2,3-dihydroxypropyl)acetamido}-2,4,6-triiodo-3-{N-(2,3-dihydroxypropyl)}carbamoyl benzoic acid (21) into: 5-{N-(2,3-diacetoxypropyl)acetamido}-2,4,6-triiodo-3-{N-(2,3-diacetoxypropyl)}carbamoyl benzoic acid (22)

The title compound (21, 114 g, 0.148 moles) oil, was diluted with pyridine (11.7 g, 0.148 moles) and acetic anhydride (605 g, 5.92 moles) and stirred at 65°–70° C. for 2 hr. The reaction was distilled to an oil, azeotroped with butyl acetate (2×100 ml), and partitioned between water (300 ml) and 3:1 toluene:ethyl acetate (200 ml). The water layer was extracted with 3:1 toluene:ethyl acetate (3×100 ml) and acidified with HCl (22.5 ml) in the presence of ethyl acetate (300 ml). The acidified $H_2O$ layer was separated and extracted twice with ethyl acetate (100 ml). The three latter ethyl acetate extracts were combined, dried over $MgSO_4$, filtered, and evaporated to a solid product (22, 118 g, 87% yield).

EXAMPLE 23

Chlorination of 5-{N-(2,3-diacetoxypropyl)acetamido}-2,4,6-triiodo-3-{N-(2,3-diacetoxypropyl)}carbamoyl benzoic acid (22) into: 5-{N-(2,3-diacetoxypropyl)acetamido}-2,4,6-triiodo-3-{N-(2,3-diacetoxypropyl)}carbamoyl benzoyl chloride (23)

The title compound (22, 113.6 g, 0.124 moles) was dissolved in ethyl acetate (100 ml) at 55° C.; thionyl chloride (44 g, 0.37 moles) was added dropwise and the mixture was refluxed for 2 hr, rotavaped to an oil, and then azeotroped with butyl acetate (2×50 ml) to give a foam which was dissolved in chloroform (200 ml) and extracted with 0.2M pH 6.7 phosphate buffer (100 ml). The organic layer was dried over $MgSO_4$, filtered, and evaporated to a solid product (23, 115 g, 98% yield).

EXAMPLE 24

Amidation of 5-{N-(2,3-diacetoxypropyl)acetamido}-2,4,6-triiodo-3-{N-(2,3-diacetoxypropyl)}carbamoyl benzoyl chloride (23) into: 5-{N-(2,3-diacetoxypropyl)acetamido}-2,4,6-triiodo-3-{N-(2,3-diacetoxypropyl)}carbamoyl benzamide (24)

The title compound (23, 105 g, 0.111 moles) was dissolved in acetonitrile (400 ml) to which anhydrous ammonia was added by utilizing a dry ice condenser at 25° C. After 3 hr of $NH_3$ reflux, the reaction was complete. Salts were filtered off, and evaporation yielded a solid product (24, 98.8 g, 96% yield).

EXAMPLE 25

Deacetylation of 5-{N-(2,3-diacetoxypropyl)acetamido}-2,4,6-triiodo-3-{N-(2,3-diacetoxypropyl)}carbamoyl benzamide (24) into: 5-{N-(2,3-dihydroxypropyl)acetamido}-2,4,6-triiodo-3-(N-{2,3-dihydroxypropyl)}carbamoyl benzamide (19)

The title compound (24, 98.7 g, 0.106 moles) was dissolved in methanol (250 ml) to which 25% w/w sodium methoxide in methanol (2.30 g, 0.0106 moles) was added at 25° C. After 15 min, the solution was distilled under vacuum to an oil, reconstituted with methanol (200 ml) and then stirred with Dowex 50 $H^+$ resin (6.0 g) until the pH decreased from 12 to 6. The resin was filtered off to produce a solution that was distilled to a foam, reconstituted with water (320 ml) and Norit SX charcoal (3.0 g), refluxed for 7 hr, filtered, deionized by stirring with Dowex 50 $H^+$ resin (3 g) and Dowex XUS-40123 $OH^-$ resin (12 g), filtered, and evaporated to the solid product (19, 79.2 g, 96% yield).

EXAMPLE 26

Methoxyacetylation of 5-amino-2,4,6-triiodo-3-{N-(1,3,4-trihydroxy-threo-but-2-yl)}carbamoyl benzamide (9) with methoxyacetyl chloride into: 5-methoxyacetylamino-2,4,6-triiodo-3-{N-(1,3,4-trihxdroxy-threo-but-2-yl)}carbamoyl benzamide (25)

The title compound (9, 100 g, 0.15 moles) was suspended in N,N-dimethylacetamide (250 ml) at 25° C. to which was added methoxyacetyl chloride (68 ml, 0.75 moles) over 30 min. The reaction mixture was stirred at 35° C. for 5 hr, when HPLC indicated that the reaction was complete. The reaction mixture was quenched with sodium methoxide (97 g, 0.45 moles) and the mixture was stirred at 40° C. for 2 hr. The solution was neutralized with Dowex 50W-X4 resin, filtered and diluted with n-butanol (700 ml). A white precipitate formed immediately and was filtered to obtain an off-white solid (25, 80.6 g, 0.11 moles, 73% yield).

EXAMPLE 27

Alkylation of Ioxithalamic Acid (26) to: 5-{N-(2,3-dihydroxypropyl)acetamido}-2,4,6-triiodo-3-{N-(2-hydroxyethyl)}carbamoyl sodium benzoate (27)

Ioxithalamic acid (26, 966 g, 1.5 moles) was dissolved in 1N sodium hydroxide (1.5 L) at room temperature, warmed to 75° C., and 3-chloro-1,2-propanediol (223.8 g, 2.03 moles) and 5N sodium hydroxide (approximately 0.4 L) were added simultaneously over 1.25 hours. The reaction was heated at 80°–90° C. for a further 2.5 hours, at which point HPLC showed completion of the reaction (ca. 90% conversion to product).

The reaction mixture was neutralized with concentrated hydrochloric acid (ca. 3 ml) and evaporated. About half of the foamy residue was taken up in water (0.4 L). On cooling, a white, crystalline solid precipitated, which was filtered and washed with ice cold water. Drying gave the crystalline product (27, 249 g).

EXAMPLE 28

Acetylation of 5-{N-(2,3-dihydroxypropyl)acetamido}-2,4,6-triiodo-3-{N-(2-hydroxyethyl)}carbamoyl-sodium benzoate (27) to: 5-{N-(2,3-diacetoxypropyl)acetamido}-2,4,6-triiodo-3-{N-(2-acetoxyethyl)}carbamoyl-benzoic acid (28)

The title compound (27), 50 g, 0.067 moles) was added to stirred acetic anhydride (102 ml, 1.080 moles, 16.0 eq.) at 25° C. Pyridine (5.4 ml, 0.067 moles, 1.0 eq.) was added and the temperature was raised to 85° C. for 1 hour when TLC indicated the reaction had gone to completion. The homogeneous reaction mixture was evaporated in vacuo to a thick oil, dissolved in butyl acetate (50 ml) and repeatedly evaporated. The oil was dissolved in $H_2O$ (260 ml) and extracted with toluene:ethyl acetate (2:1; 4×100 ml). The aqueous layer was acidified with 12N hydrochloric acid (11 ml) and extracted with ethyl acetate (3×50 ml). The organic layer was dried over magnesium sulfate, evaporated to a foam (28) and taken directly to the next step (55 g, 0.065 moles, 97% yield).

EXAMPLE 29

Chlorination of 5-{N-(2,3-diacetoxypropyl) acetamido}-2,4,6-triiodo-3-{N-(2-acetoxy-ethyl) }carbamoyl-benzoic acid (28) to: 5-{N-(2,3-diacetoxypropyl)acetamido}-2,4,6-triiodo-3-{N-(2-acetoxyethyl)}carbamoyl-benzoyl chloride (29)

The title compound (28, 55 g, 0.065 moles) was dissolved in 1,2-dichloroethane (170 ml) and heated to 85° C. Thionyl chloride (9.8 ml, 0.134 moles, 2.0 eq.) was added and TLC indicated the reaction had reached completion after 3 hours. The reaction mixture was evaporated in vacuo to an oil, redissolved in butyl acetate (50 ml) and repeatedly evaporated. The product was isolated as a yellow foam (29), 51.9 g, 0.060 moles, 92% yield).

EXAMPLE 30

Amidation of 5-{N-(2,3-diacetoxypropyl) acetamido}-2,4,6-triiodo-3-{N-(2-acetoxyethyl) }carbamoyl-benzoyl chloride (29) to: 5-{N-(2,3-diacetoxypropyl)acetamido}-2,4,6-triiodo-3-{N-(2-acetoxyethyl)}carbamoyl-benzamide (30)

The title compound (29, 51.9 g, 0.060 moles) was dissolved in acetonitrile (200 ml) and anhydrous ammonia (excess) was added at 10° C. After 4 hours, TLC indicated the reaction was complete. The reaction mixture was filtered to remove ammonium chloride salts and the solvent was removed to give a yellow oil (30, 47 g, 0.056 moles, 93% yield).

EXAMPLE 31

Deacetylation of 5-{N-(2,3-diacetoxypropyl) acetamido}-2,4,6-triiodo-3-{N-(2-acetoxyethyl) }carbamoyl-benzamide (30) to: 5-{N-(2,3-dihdroxypropylacetamido)}-2,4,6-triiodo-3-{N-(2-hdroxyethy)}carbamoyl-benzamide (31)

The title compound (30, 47 g, 0.056 moles) was dissolved in methanol (240 ml) and 25% sodium methoxide (3.9 g, 0.3 eq.) was added to raise the pH to ca. 12. The solution was stirred at 25° C. for 1 hour when HPLC indicated the deacetylation was complete. The reaction mixture was neutralized with 1N HCl (10 ml) and solvent removal gave an off-white foam (31, 39 g, 0.054 moles, 97% yield, 98% pure), which was recrystallized from hot methanol (5 g in 15 ml, with seeding).

EXAMPLE 32

Amidation of 5-amino-2,4,6-triiodoisophthaloyl chloride (32) into: 5-amino-2,4,6-triiodo-3-chlorocarbonyl-benzamide (33)

The starting material (32, 300 g, 0.503 moles) was dissolved in tetrahydrofuran (900 ml) and the homogeneous solution cooled in ice to 5°–10° C. Concentrated ammonium hydroxide (92.3 ml, 1.38 moles) was added over 10 minutes; the temperature rose to 30° C.

The reaction mixture was stirred at room temperature for a total of 90 hours, with further additions of ammonium hydroxide (total 25.2 ml, 0.38 moles), then it was cooled and the insoluble salts removed by filtration. The filtrate was washed with saturated NaCl (200 ml×2).

The tetrahydrofuran was evaporated to give a viscous oil. Ethyl acetate (800 ml) precipitated a tan solid which was filtered, washed with ethyl acetate (100 ml×2) and dried to give (33, 193 g, 66.5% yield).

EXAMPLE 33

Dimerization of 5-amino-2,4,6-triiodo-3-chlorocarbonyl-benzamide (33) into: Malonic Acid-bis-{(3-chlorocarbonyl-5-carbamoyl)-2,4,6-triiodanilide} (34)

The title compound (33, 20.0 g, 34.7 mM) was dissolved in dry tetrahydrofuran (100 ml), heated to 45° C., and malonyl dichloride (2.53 ml, 26 mM) was added over 3 minutes to give a heterogeneous mixture. Dry THF (100 ml) was added, and the suspension stirred for 1 hour when TLC showed the reaction to be complete. The mixture was diluted with butyl acetate (150 ml), and the solid was filtered, washed with butyl acetate (50 ml×2) and dried in vacuo to give the product (34, 13.18 g, 62% yield).

EXAMPLE 34

Amidation of Malonic Acid-bis-{(3-chlorocarbonyl-5-carbamoyl)-2,4,6-triiodoanilide} (34) into: Malonic Acid-bis-[{3-N-(1,3,4-trihydroxy-threo-but-2-yl-carbamoyl-5-carbamoyl}-2,4,6-triiodoanilide] (35)

The title compound (34, 8.0 g, 6.56 mM) was dissolved in dry N,N-dimethyl-acetamide (10 ml), triethylamine (1.83 ml, 13.12 mM) was added and the solution was cooled to 20° C. Trans-5-amino-2,2-dimethyl-6-hydroxy-1,3-dioxepan (2.64 g, 16.4 mM) was added over 3 minutes, and the homogeneous mixture was stirred at room temperature for 6 hours, when TLC indicated the reaction was complete. The solvent was evaporated, water (50 ml) was added, and the mixture was heated at 75° C. for 15 minutes to cleave the acetonides. The product was obtained by evaporation and precipitation with isopropanol (100 ml). The solid was filtered, washed with isopropanol (20 ml×2) and dried to give 8.6 g (35, 94% yield).

EXAMPLE 35

Amidation of 5-N-methylamino-2,4,6-triiodoisophthaloyl-chloride (36) to: 5-N-methylamino-2,4,6-triiodo-3-chlorocarbonyl-benzamide (37)

The starting material (36, 385 g, 0.5 moles) was dissolved in tetrahydrofuran (1 L) and cooled to 10° C. Concentrated ammonium hydroxide (100 ml, 1.5 moles) was added over 5 minutes; the temperature rose to ca. 25° C.

The reaction mixture was stirred at room temperature for 65 hours, with additional portions of concentrated $NH_4OH$ added at 20 hours (3.5 ml) and 44 hours (3.5 ml).

Upon cooling, the insoluble salts and bisamide were filtered and the THF filtrate washed with saturated sodium chloride solution (100 ml×2).

The THF was evaporated and the product precipated from the thick oil by ethyl acetate (500 ml). Filtration, washing with ethyl acetate and drying gave (37, 132.1 g, 45% yield).

EXAMPLE 36

Dimerization of 5-N-methylamino-2,4,6-triiodo-3-chlorocarbonyl-benzamide (37) into: Malonic Acid-bis-{(3-chlorocarbonyl-5-carbamoyl)-2,4,6-triiodo-N-methyl anilide} (38)

The title compound (37, 25 g, 42.3 mM) was dissolved in dry tetrahydrofuran (100 ml) and the homogeneous solution was heated to 50° C. Malonyl dichloride (3.05 ml, 31.3 mM) was added over 2 minutes, followed by additional tetrahydrofuran (50 ml) and the suspension was heated for one hour, when TLC showed the reaction was complete.

Upon dilution with butyl acetate (50 ml), the product was filtered, washed with butyl acetate (25 ml×2) and dried to give an off-white solid (38, 15.24 g, 58% yield).

EXAMPLE 37

Transformation of Malonic Acid-bis-{(3-chlorocarbonyl-5-carbamoyl)-2,4,6-triiodo-N-methyl anilide} (38) into: Malonic Acid-bis-[{3-N-(1,3,4-trihydroxy-threo-but-2-yl-carbamoyl) 5-carbamoyl}-2,4,6-triiodo-N-methyl anilide] (39)

The starting material (38, 10 g, 8 mM) was dissolved in dry N,N-dimethyl-acetamide (15 ml) and triethylamine (2.23 ml, 16 mM). Trans-5-amino-2,2-dimethyl-6-hydroxy-1,3-dioxepan (aminodioxepan) (3.22 g, 20 mM) was added over 5 minutes, and the homogeneous mixture was stirred for 8 hours, when TLC showed the reaction to be complete.

The DMA was removed by vacuum distillation and the isopropylidenes were cleaved with aqueous hydrochloric acid at 50° C. The water was removed on the rotary evaporator and isopropanol added to precipitate the product. Filtration, washing with isopropanol (10 ml×3), and drying gave the dimer (39, 9.86 g, 87% yield).

EXAMPLE 38

5-N-(methyl)amino-2,4,6-triiodo-3-chlorocarbonyl-benzamide (36) into: 5-{N-(methyl)-2-acetoxyacetamido}-2,4,6-triiodo-3-chlorocarbonyl-benzamide (40)

The starting material (36, 25 g, 42.3 mM) was dissolved in dry N,N-dimethyl-acetamide (50 ml) at room temperature. 2-Acetoxyacetyl chloride (6.83 ml, 63.5 mM) was added, and after stirring overnight, TLC indicated the reaction was complete.

The product was precipitated by the addition of ice-cold water (200 ml) and filtered. After washing with water the solid was dissolved in tetrahydrofuran (200 ml), and the solution extracted with saturated NaCl:saturated $NaHCO_3$ (3:1, 250 ml), followed by saturated NaCl (100 ml). The organic layer was dried ($MgSO_4$) and the solvent removed to give a foam (40, 22.1 g, 77.2% yield).

EXAMPLE 39

Amidation and Deprotection of 5-{N-(methyl)-2-acetoxyacetamido}-2,4,6-triiodo-3-chlorocarbonyl-benzamide (40) into: 5-{N-(methyl)-2-hydroxyacetamido}-2,4,6-triiodo-3-{N-(1,3,4-trihydroxy-three-but-2-yl)}carbamoyl-benzamide (41)

The title compound (40, 7.0 g, 10.35 mM) was dissolved in a mixture of tetrahydrofuran (40 ml) and triethylamine (1.44 ml, 10.35 mM) and cooled to 10° C. Solid aminodioxepan (2.0 g, 12.41 mM) was added, the cooling was removed and the reaction was allowed to stir at 25° C. By 18 hours, TLC indicated reaction completion. The reaction mixture was diluted with tetrahydrofuran (40 ml) and saturated NaCl:saturated $NaHCO_3$ (3:1, 50 ml) and the layers were separated. The organic layer was washed with saturated NaCl (40 ml×2), dried ($MgSO_4$) and the solvent evaporated to give a foam (6.9 g, 82% yield).

The foam was dissolved in methanol (50 ml) and 4.6 formal NaOMe solution (0.5 ml) added. The solution was stripped at 50° C. to yield an oil which was subsequently mixed with water (50 ml) and Dowex 50 $H^+$ resin (10 g). Heating at 60° C. for 30 minutes eventually gave a homogeneous solution, and HPLC indicated that ester and isopropylidene cleavage was complete.

The resin was filtered, and the solution cycled through sequential Duolite A 340 $OH^-$/Dowex 50 $H^+$ columns until deionization was complete. The compound was eluted from the columns with water and subsequently treated with Norit Ultra S-X carbon (0.4 g). After 1 hour at 70° C., the carbon was filtered and the water evaporated to yield a white foam (41, 3.8 g, 50% yield from 40).

EXAMPLE 40

Acetoxyacetylation of 5-amino-2,4,6-triiodo-3-chlorocarbonyl benzamide (33) into: 5-acetoxyacetylamino-2,4,6-triiodo-3-chlorocarbonyl benzamide (42)

The starting material (33, 200 g, 0.347 moles) in 1200 ml dioxane was heated to 60° C. Acetoxyacetyl chloride (142 g, 1.041 moles) was added dropwise over 15 minutes at which time the reaction was heated to 90° C. and held there for 6.5 hours. After cooling to 15° C. the solid product (42) was filtered, washed with 4×100 ml dioxane and vacuum dried to a weight of 200.5 g (yield 85%).

EXAMPLE 41

Amidation of 5-acetoxyacetylamino-2,4,6-triiodo-3-chlorocarbonyl benzamide (42) into: 5-acetoxyacetylamino-2,4,6-triiodo-3-{N-(2,3-dihydroxypropyl)}carbamoyl benzamide (43)

The starting material (42, 118 g, 0.174 moles) was added to a flask containing N,N-dimethyl acetamide (180 ml), 3-amino-1,2-propanediol (24.2 g, 0.266 moles) and triethylamine (18.0 g, 0.177 moles). The reaction was held at 25° C. for 4 hours and was then diluted by the dropwise addition of n-pentanol (1080 ml) during vigorous mechanical stirring. The resulting precipitate (43) was filtered, washed with 4×100 ml n-pentanol, and vacuum dried to a weight of 124.9 g (crude yield 98%).

EXAMPLE 42

Deacetylation of 5-acetoxyacetylamino-2,4,6-triiodo-3-{N-(2,3-dihydroxypropyl)}carbamoyl benzamide (43) into: 5-hydroxyacetylamino-2,4,6-triiodo-3-{N-(2,3-dihydroxypropl)}carbamoyl benzamide (44)

The starting material (43, 124.8 g, 0.170 moles) was dissolved in methanol (1.5 L) and water (0.5 L) and than treated with Dowex 50 $H^+$ and Biotex $5^-OH$ ion exchange resins. The resins were removed with a sieve after 20 hours of stirring and the resulting mixture was distilled under reduced pressure to a solid residue. Methanol (400 ml) and 25% w/w sodium methoxide in methanol (36.9 g, 0.17 moles) were added to the residue to produce a solution which was filtered, distilled under pressure to remove methyl acetate, diluted with methanol, neutralized with concentrated HCl and then distilled under reduced pressure to a solid consisting of 9.9 g NaCl and 94.0 g of the product (44). The yield was 80%.

EXAMPLE 43

Protection of 5-hydroxyacetylamino-2,4,6-triiodo-3-{N-(2,3-dihydroxypropyl)}carbamoyl benzamide (44) with 3,4-dihydro-2H-pyran into: 5-(2-tetrahydropyranyloxy)acetylamino-2,4,6-triiodo-3-{N-(2,3-tetrahydropyranyloxy)propyl}carbamoyl benzamide (45)

The starting material (44, 3.44 g, 5 mMoles) was mixed with dioxane (15 ml) and methanesulfonic acid (29.6 mg=0.31 mMoles). 3,4-Dihydro-2H-pyran (3.36 g, 40 mMole) was added and the mixture was stirred at 25° C. for 4 days. The reaction was filtered, basified with triethylamine (62 mg, 0.62 mMmole), distilled under reduced pressure to an oil, reconstituted with methanol, and distilled under reduced pressure to a product residue (45) which was carried directly into alkylation.

EXAMPLE 44

Alkylation and Deprotection of 5-(2-tetrahydropyranyloxy)acetylamino-2,4,6-triiodo-3-{N-(2,3-tetrahydropyranyloxy)propyl}carbamoyl benzamide (45) into: 5-{N-(2-hydroxyethyl) hydroxyacetamido}-2,4,6-triiodo-3-{N-(2,3-dihydroxypropyl)}carbamoyl benzamide (46)

The starting material (45, 5.0 mMole), a semisolid residue from the previous step, was mixed with methanol (18 ml), trisodium phosphate dedecahydrate (4.75 g, 12.5 mMoles) and chloroethanol (805 mg, 10 mMoles). The resulting suspension was stirred at 40°–45° C. for 31 hours, filtered and diluted with 0.5 ml concentrated HCl. The acidified filtrate was distilled under reduced pressure to an oil and reconsitituted with 0.01N HCl (20 ml) and methanol (20 ml). After repeating this twice more, the acidic solution was finally distilled under reduced pressure to solid product (46) weighing 3.50 g, yield 95%.

EXAMPLE 45

Alkylation of 3,5-diacetylamino-2,4,6-triiodobenzoic acid (diatrizoic acid, 47) into: Sodium 3,5-{N,N'-(2,3-dihydroxypropyl) diacetamido}-2,4,6-triiodobenzoate (48)

To a suspension of the starting material (47, 50 g, 0.079 moles) in methanol (300 ml) was added trisodium phosphate dodecahydrate (149 g, 0.393 moles) and 3-chloro-1,2-propanediol (35 g, 0.314 moles) and the reaction was heated at 40° C. for 24 hours. Insoluble salts were removed by vacuum filtration, the filtrate was neutralized with HCl and evaporated to a white foam (48, ca. 59 g, yield 94% including 10% ester byproduct). The foam was taken directly into acetylation.

EXAMPLE 46

Acetylation of Sodium 3,5-{N,N'-(2,3-dihydroxypropyl)diacetamido}-2,4,6-triiodobenzoate (48) into: 3,5-{N,N'-(2,3-diacetoxypropyl) diacetamido}-2,4,6-triiodobenzoic acid (49)

The starting material (48, 59 g, 0.075 moles) was mixed with acetic anhydride (150 ml, 1.58 moles) and pyridine (6 ml, 0.075 moles) and heated to 85° C. for 1 hour. The acetic anhydride, acetic acid, and pyridine were removed by distillation at 70°–80° C., and the yellow foam was azeotroped with butyl acetate (50 ml×x2).

The product (sodium salt of 49) was dissolved in water (300 ml) and extracted with a 2:1 mixture of toluene and ethyl acetate (150 ml×3) to remove the ester byproduct from the previous alkylation step. The aqueous solution was acidified with concentrated HCl to pH 2.5 and the white precipitate was extracted with ethyl acetate (75 ml×2). The combined organic extracts were dried over magnesium sulfate and the solvent removed to give a yellow oil (49, ca. 58 g, 83% yield overall from 47). The product was taken directly into chlorination.

EXAMPLE 47

Chlorination of 3,5-{N,N'-(2,3-diacetoxypropyl) diacetamido}-2,4,6-triiodobenzoic acid (49) into: 3,5-{N,N'-(2,3-diacetoxypropyl)diacetamido}-2,4,6-triiodobenzoyl chloride (50)

To the starting material (49, ca. 0.062 moles) in ethyl acetate (125 ml) was added thionyl chloride (23 ml, 0.32 moles) at 65°–70° C., and the temperature increased to 75°–80° C. for 1 hour. TLC indicated that the reaction was complete and thionyl chloride and ethyl acetate were removed under vacuum. The residue was azeotroped with butyl acetate (150 ml×2) and the resultant solid dried. The tan foam (50, ca. 56 g, yield 95%) was taken directly into the subsequent amidation step.

EXAMPLE 48

Amidation of 3,5-{N,N'-(2,3-diacetoxypropyl) diacetamido}-2,4,6-triiodobenzoyl chloride (50) into: 3,5-{N,N'-(2,3-diacetoxypropyl)diacetamido}-2,4,6-triiodo-benzamide (51)

To the starting material (50, ca. 0.059 moles) in acetonitrile (200 ml) was added anhydrous amnonia (excess) at 10° C., and the temperature was increased to 25° C. for 5 hours. The reaction was complete by TLC and the ammonium chloride was removed by filtration. The filtrate was evaporated to a yellow foam (51, 53 g, estimated yield 97%). The foam was taken directly to deacetylation.

EXAMPLE 49

Deacetylation of 3,5-{N,N'-(2,3-diacetoxypropyl) diacetamido}-2,4,6-triiodobenzamide (51) into: 3,5-{N,N'-(2,3-dihydroxypropyl)diacetamido}-2,4,6-triiodobenzamide (52)

A solution of the starting material (51, ca 0.057 moles) in methanol (250 ml) was mixed with sodium methoxide (4.6 molal, 5.0 g, 0.023 moles) and was stirred at room temperature for 30 minutes. HPLC showed that the deacetylation was complete and the reaction mixture was neutralized with concentrated HCl. The insoluble sodium chloride was removed by filtration and the filtrate was evaporated to a yellow foam (52, 43 g, yield 97%, purity 98% by HPLC).

Synthesis of Malonic acid bis[{3-N-(2,3-dihydroxypropyl-carbamoyl) 5-carbamoyl}-2,4,6-triiodo-N-(2,3-dihydroxypropyl)]anilide A) 5-amine-2,4,6-triiodo-3-chlorocarbonyl benzamide (1)

To a suspension of 5-amino-2,4,6-triiodoisophthalamic acid (53.0 g, 0.1 mol) in 265 ml of ethyl acetate, 21.9 ml (0.3 mol) of thionyl chloride was added and heated at reflux temperature for 4 hours. After this time, the reaction was quenched by adding 6 ml of water, and the solvent was distilled near to dryness. The residue was filtered off, washed with ethyl acetate and dried "in vacuo". 47 g (80%) of pure acid chloride (1) were obtained.

IR (KBr) 3450, 3305, 1770, 1680, 1661, 1589, 1389, 1021 $cm^{-1}$.

$^1$H NMR (DMSO-$d_6$) σ: 3.5 (br s, 2H, Ar—$NH_2$), 7.6–8.1 (m, 2H, Ar—$CONH_2$).

$^{13}$C NMR (DMSO-$d_6$) σ: 171.62, 171.15, 170.19, 169.82 (CO); 151.35, 149.67, 149.61, 148.02, 147.61, 143.71 (Ar); 98.52, 96.75, 89.18, 80.44, 78.44, 72.36 (Ar—I).

B) N,N'-Bis-(3-chlorocarbonyl-5-carbamoyl-2,4,6-triiodophenyl)malonamide (2)

A suspension of 45.0 g (0.078 mol) of acid chloride (1) in 135 ml of dry dioxane was heated at 90° C., and 4.6 ml (0.047 mol) of malonyl chloride were added with vigorous stirring. The mixture was stirred for 45 minutes, then was cooled at room temperature and the resulting solid was filtered off, washed with dioxane and dried "in vacuo".

Yield: 38.5 g (80%)

IR (KBr) 3166, 1778, 1654, 1514, 1359 $cm^{-1}$.

$^1H$ NMR (DMSO-$_6$) σ: 3.5 (s, 2H, $CH_2$), 7.7–8.3 (m, 4H, Ar—$CONH_2$), 10.2–10.5 (m, 2H, CONH).

$^{13}C$ NMR (DMSO-$d_6$) σ: 171.09, 170.62, 169.82, 169.67, 168.46, 164.88, 164.75 (CO); 151.54, 150.93, 149.43, 149.13, 143.87, 143.71, 143.06, 142.89 (Ar); 102.47, 99.23, 97.40, 96.08, 88.51, 87.06 (Ar-1); 42.80 ($CH_2$).

C) N,N'-Bis-5-carbamoyl-3-[N-(2,3-(isopropylidendioxy) propyl)carbamoyl]-2,4,6-triiodophenyl}malonamide (3)

A mixture of 30.0 g (0.025 mol) of compound (2), 11.5 g (0.108 mol) of anhydrous sodium carbonate and 9.1 g (0.054 mol) of 2,2-dimethyl-5-aminomethyl-1,3-dioxolane hydrochloride in 200 ml of ethyl acetate was heated at reflux temperature for 48 hours. After this time, the reaction was complete, and the solid obtained was filtered off, washed with water and dried "in vacuo".

Yield: 32 g (85%)

IR (KBr) 3252, 3185, 1685, 1669, 1652, 1540, 1503, 1370, 1352, 1213 $cm^{-1}$.

$^1H$ NMR (DMSO-$d_6$) σ: 1.26 (s, 6H, $CH_3$), 1.35 (s, 6H, $CH_3$), 3.1–3.5 (m, 4H, $CH_2$—N), 3.34 (s, 2H, OC—$CH_2$—CO), 3.7–4.1 (m, 4H, $CH_2$—O), 4.1–4.3 (m, 2H, CH—O), 7.6–8.1 (m, 4H, Ar—$CONH_2$), 8.5–8.8 (m, 2H, Ar—CONH), 10.2 (br s, 2H, CONH—Ar).

$^{13}C$ NMR (DMSO-$d_6$) σ: 171.16, 169.83, 165.02 (CO); 150.63, 149.77, 143.31 (Ar); 108.53 (C of isopropyliden fragment); 98.52, 89.46 (Ar-1); 73.30 (CH—O); 67.72 ($CH_2$—O); 42.02 ($CH_2$y$CH_2$N); 27.10 ($CH_3$); 25.52 ($CH_3$).

D) Malonic acid bis[{3-N-(2,3-dihydroxypropyl-carbamoyl)5-carbamoyl}-2,4,6-triiodo-N-(2,3-dihydroxypropyl)]anilide A mixture of 34.0 g (0.024 mol) of compound (3), and 43.4 g (0.114 mol) of trisodium phosphate dodecahydrate in 170 ml of methanol was heated at 50° C. and at this temperature 8.7 ml (0.104 mol) of 3-chloro-1,2-propanediol was added and the mixture stirred for 48 hours. After this time, the reaction was considered complete, the mixture was cooled at room temperature, the inorganic salts were filtered off and the flitrate was evaporated to dryness "in vacuo". The residue was slurried with water, filtered again and dried.

Yield: 35 g (92%) of N,N'-Bis(2,3-dihydroxypropyl)-N, N'-bis-{5-carbamoyl-3-[N-(2,3-(isopropylidendioxy) propyl)carbamoyl]-2,4,6-triiodophenyl}malonamide. This product was dissolved in 200 ml of a mixture methanol-water (1:1) and hydrolyzed by treatment with concentrated hydrochloric acid at pH=1 and 50° C. for 5 hours. After this time, the mixture of reaction was neutralized to pH 6.5 and concentrated to dryness "in vacuo". The residue obtained was purified by preparative liquid chromatography (PLC) in reverse phase using a mixture of methanol and water as eluent. The purest fraction collected was evaporated to dryness "in vacuo". 22 g (60% of pure ICI 3393 were obtained.

mp. 257° C. (dec) ($H_2O$).

$R_f$=0.36 (n-BuOH—AcOH—$H_2O$, 3:2:1, (detection under UV, light),

IR (KBr) 3388, 3300, 1666, 1645, 1557, 1400, 1286, 1036 $cm^{-1}$.

$^1H$ NMR (DMSO-$d_6$) σ: 2.6–4.0 (m, 22H, $CH_2$, CH), 4.4–4.9 (m, 8H, OH), 7.3–8.9 (m, 6H, CONH, $CONH_2$).

$^{13}C$ NMR (DMSO-$d_6$) σ: 171.71, 171.40, 171.10, 169.92, 167.24, 166.95, 166.17 (CO—N); 151.47, 148.21, 147.02 (Ar); 101.04, 100.79, 100.04, 98.61, 91.66, 90.11 (Ar-1); 69.97 (CHOH); 64.68, 64.06, 63.15 ($CH_2$OH); 54.10 ($CH_2$—NAr); 42.63 (NOC—$\underline{C}H_2$—CON, CON—$\underline{C}H_2$).

MS(FAB+) m/z 1479.1 ($M^+$+H).

EXAMPLE 50

Injection solutions containing 5-{N-(2,3-dihydroxypropyl)acetamido}-2,4,6-triiodo-3-{N-(2,3-dihydroxypropyl)}-carbamoyl benzamide (19)

| Composition of 100 ml | Iodine Content of Injection Solution in mg/ml | | |
|---|---|---|---|
| Aliquots of Solution | 300 | 350 | 400 |
| Compound (g) | 58.87 | 68.68 | 78.49 |
| Disodium, calcium salt of ethylenediaminetetraacetic acid (mg) | 10 | 10 | 10 |
| Tris-(hydroxymethyl)amino-methane (mg) | 121 | 121 | 121 |
| Water for injection to volume (ml) | 100 | 100 | 100 |
| Osmolality (mOsm/kg) | 399 | 473 | 510 |
| Viscosity @ 37° C. (centipoise) | 4.1 | 6.6 | 10.6 |

Procedure: The sodium-calcium salt of ethylenediamine-tetraacetic acid, tris-(hydroxymethyl)aminomethane, and the contrast media were dissolved in water for injection and adjusted to pH 7.0 by the addition of 1 N hydrochloric acid. Solutions were QS'd to 100 ml with water for injection, filtered through a 0.22 micron membrane into glass vials, capped, and autoclaved for 20 min at 121° C.

EXAMPLE 51

Injections solutions containing 5-{N-(2-hydroxyethyl)acetamido}-2,4,6-triiodo-3-{N-(1,3,4-trihydroxy-threo-but-2-yl)}carbamoyl benzamide (11)

| Composition of 100 ml | Iodine Content of Injection Solution in mg/ml | | |
|---|---|---|---|
| Aliquots of Solution | 300 | 350 | 400 |
| Compound (g) | 58.87 | 68.68 | 78.49 |
| Disodium, calcium salt of ethylenediaminetetraacetic acid (mg) | 56 | 56 | 56 |
| Trisodium citrate (mg) | 77 | 77 | 77 |
| Water for injection to volume (ml) | 100 | 100 | 100 |
| Osmolaity (mOsm/kg) | 301 | 337 | 370 |
| Viscosity at 37° C. (centipoise) | 4.2 | 6.6 | 13.1 |

Procedure: The calcium-disodium salt of ethylenediaminetetraacetic acid, trisodium citrate, and the contrast media were dissolved in water for injection and adjusted to pH 5.0 to 6.0 with sodium carbonate and carbon dioxide. Solutions were QS'd to 100 ml with water for injection, filtered through a 0.22 micron membrane into glass vials, capped and autoclaved for 20 minutes at 121° C.

It is evident from the above results, that novel non-ionic contrast media are provided having substantially superior properties to compounds presently available. Because of the improvement in the physical characteristics, particularly as to osmolality and viscosity, a broad range of body regions may be diagnosed while providing for easy administration and lower pain. Despite the large number of compounds which have been synthesized and tested, the subject compounds are found to be superior to previously disclosed compounds. By providing for three different nitrogens in the molecule, only two of which are substituted, the novel properties are achieved. In addition, synthetic routes are provided which are efficient and provide for high yields, while allowing for the use of readily available materials.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

I claim:

1. A non-ionic contrast medium compound of the formula:

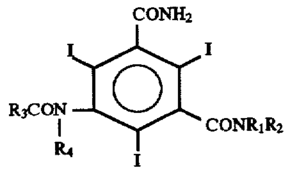

having at least two hydroxy groups; and wherein $R_1$ is hydrogen, alkyl or hydroxyalkyl, wherein alkyl is of from 1 to 6 carbon atoms;

$R_2$ is hydroxyalkyl of from 2 to 6 carbon atoms having from 1 to n−1 hydroxyl groups, wherein n is the number of carbon atoms;

$R_3$ is alkyl, hydroxyalkyl or alkoxyalkyl, each of from 1 to 6 carbon atoms, or $R_3$ is a bridge of from 0 to 2 carbon atoms terminating in a group of the formula

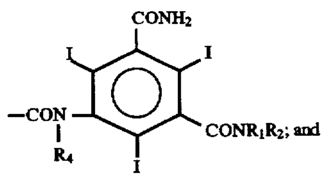

$R_4$ is hydrogen, or alkyl of from 1 to 6 carbon atoms having from 0 to n−1 hydroxyl groups, wherein n is the number of carbon atoms;

with the proviso that said compound is not S-(−)-3-N-[2-hydroxy-1-(hydroxymethyl)ethyl]-5-[(2-hydroxy-1-oxopropyl)amino]-2,4,6-triiodoisophthalamic acid amide.

2. A compound according to claim 1, wherein $R^2$ is of 4 carbon atoms and three hydroxyl groups, $R_3$ is other than taken together to form a bridge and $R_4$ is of from two to three carbon atoms and has at least one hydroxyl group.

3. A compound according to claim 1, wherein $R_2$ is of 3 carbon atoms and 2 hydroxyl groups, $R_3$ is other than taken together to form a bridge, and $R_4$ is of 3 carbon atoms and 2 hydroxyl groups.

4. A compound according to claim 3, wherein $R_2$ and $R_4$ are the same.

5. A radiologic formulation comprising a compound according to claim 1 in a physiologically acceptable carrier.

6. In a method for taking a non-invasive determination of a physiologic state using irradiation and a non-ionic contrast medium;

the improvement which comprises employing a non-ionic contrast medium containing a compound according to claim 1.

7. A compound of claim 1, wherein $R_1$ is H, $C_{1-3}$-alkyl or $C_{2-6}$-hydroxyalkyl; $R_2$ is $C_{2-4}$-hydroxyalkyl; $R_3$ is $C_{1-3}$-alkyl, $C_{1-4}$-hydroxyalkyl or $C_{1-3}$-alkoxy-$C_{1-3}$-alkyl; and $R_4$ is H, $C_{1-4}$-alkyl or $C_{1-4}$hydroxyalkyl.

8. In a method of obtaining an X-ray image comprising administering an X-ray contrast agent, the improvement wherein the agent is a compound of claim 1.

9. The compound of claim 1, wherein $R_3$ is a bridge of from 0 to 2 carbon atoms terminating in a group of the formula:

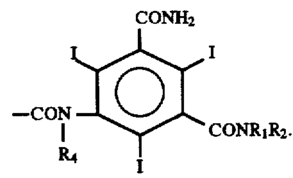

10. The compound of claim 1, which is malonic acid bis[{3-N-(2,3-dihydroxypropyl-carbamoyl) 5-carbamoyl}-2,4,6-triiodo-N-(2,3-hydroxypropyl)]anilide; malonic acid bis[{3-N-(2,3-dihydroxypropyl-carbamoyl) 5-carbamoyl}-2,4,6-triiodo-N-(2-hydroxyethyl)]anilide; malonic acid bis[{3-N-(1,3,4-trihydroxybut-2-yl-carbamoyl) 5-carbamoyl}-2,4,6-triiodo-N-methyl]anilide; or, malonic acid bis[{3-N-(1,3,4-trihydroxybut-2-yl-carbamoyl) 5-carbamoyl}-2,4,6-triiodo]anilide.

11. The compound of claim 1, which is malonic acid bis[{3-N-(2,3-dihydroxypropyl-carbamoyl) 5-carbamoyl}-2,4,6-triiodo-N-(2,3-hydroxypropyl)]anilide.

12. The compound of claim 1, wherein $R_2$ is hydroxyalkyl having 1 to 4 hydroxyl groups.

13. The compound of claim 1, wherein $R_2$ is hydroxyalkyl having 1 to 3 hydroxyl groups.

14. The compound of claim 1, wherein $R_3$ is hydroxyalkyl or alkoxyalkyl.

15. 5-{N-(2-hydroxyethyl)acetamido}-2,4,6-triiodo-3-{N-(1,3,4-trihydroxy-threo-but-2-yl)}carbamoyl benzamide.

16. 5-{N-(2,3-dihydroxypropyl)acetamido}-2,4,6-triiodo-3-{N-(2,3-dihydroxypropyl)}carbamoyl benzamide.

17. 5-{N-(2,3-dihydroxypropyl)acetamido}-2,4,6-triiodo-3-{N-(2-hydroxyethyl)}carbamoyl benzamide.

18. 5-{N-(methyl)-2-hydroxyethylacetamido}-2,4,6-triiodo-3-{N-(1,3,4-trihydroxy-threo-but-2-yl)}carbamoyl benzamide.

19. Malonic Acid-bis-[3-{N-(1,3,4-trihydroxy)-threo-but-2-yl}carbamoyl-5-carbamoyl]-2,4,6-triiodo-N-(methyl)-anilide.

20. A radiologic formulation comprising a compound according to claim 15 in a physiologically acceptable carrier.

21. A radiologic formulation comprising a compound according to claim 16 in a physiologically acceptable carrier.

22. In a method of obtaining an X-ray image comprising administering an X-ray contrast agent, the improvement wherein the agent is a compound of claim 15.

23. The compound of claim 1, which is 5-{N-(2,3-dihydroxypropyl)acetamido}-2,4,6-triiodo-3-{N-(1,3,4-trihydroxy-threo-but-2-yl)}carbamoyl benzamide.

24. A radiologic formulation comprising a compound according to claim 23 in a physiologically acceptable carrier.

* * * * *